United States Patent [19]

Stapp

[11] 4,216,119
[45] Aug. 5, 1980

[54] CATALYST SYSTEM COMPRISING ELEMENTAL SULFUR OR A SULFUR HALIDE FOR CONVERSION OF DIENES OR MONOOLEFINS TO DIESTERS

[75] Inventor: Paul R. Stapp, Bartlesville, Okla.

[73] Assignee: Phillips Petroleum Company, Bartlesville, Okla.

[21] Appl. No.: 16,751

[22] Filed: Mar. 1, 1979

Related U.S. Application Data

[62] Division of Ser. No. 827,641, Aug. 25, 1977, Pat. No. 4,162,363.

[51] Int. Cl.$^2$ .................... B01J 31/02; B01J 31/04; B01J 27/02; B01J 27/06
[52] U.S. Cl. ................ 252/429 R; 252/428; 252/439
[58] Field of Search .............. 252/429R, 426, 428, 252/439, 441; 560/246

[56] References Cited

U.S. PATENT DOCUMENTS

| | | | |
|---|---|---|---|
| 2,695,313 | 11/1954 | Toland, Jr. | 562/527 |
| 2,870,196 | 1/1959 | Barney | 560/190 |
| 2,903,480 | 9/1959 | Toland | 562/411 |
| 2,985,521 | 5/1961 | Herman et al. | 44/68 |
| 3,119,874 | 1/1964 | Paszthory et al. | 260/597 B |
| 3,119,875 | 1/1964 | Steinmetz et al. | 260/597 B |
| 3,368,505 | 2/1968 | Harrison | 110/246 |
| 3,479,395 | 11/1969 | Huguet | 560/246 |
| 3,634,496 | 1/1972 | Kominami et al. | 560/245 |
| 3,778,468 | 12/1973 | Kollar | 560/246 |
| 3,904,591 | 9/1975 | Fischer | 252/441 |
| 4,026,924 | 5/1977 | Stapp | 560/246 |

FOREIGN PATENT DOCUMENTS 1368505  9/1974  United Kingdom.

OTHER PUBLICATIONS

Suzuki; Ind. Eng. Chem. Prod. Res. Dev.; 10, pp. 179-183 (1971).
Hill; Chem. Rev. 61, pp. 537-562 (1961).

*Primary Examiner*—P. E. Konopka

[57] ABSTRACT

Conjugated dienes or monoolefins are converted to diesters in a process utilizing a catalyst system comprising an alkali metal compound and a sulfur source comprising elemental sulfur or a sulfur halide, optionally with a halide source, in carboxylic acid media.

18 Claims, No Drawings

CATALYST SYSTEM COMPRISING ELEMENTAL SULFUR OR A SULFUR HALIDE FOR CONVERSION OF DIENES OR MONOOLEFINS TO DIESTERS

This is a divisional application of Ser. No. 827641 filed Aug. 25, 1977, now U.S. Pat. No. 4,162,363 Patented July 24, 1979.

FIELD OF THE INVENTION

The invention pertains to the conversion of conjugated dienes to diesters. In another aspect, the invention pertains to the conversion of monoolefins to diesters. In a further aspect, the invention pertains to a sulfur-based catalyst system.

BACKGROUND OF THE INVENTION

Conjugated dienes and monoolefins such as butadiene or ethylene, present intriguing possible sources of a variety of more valuable chemicals, valuable intermediates and end-products. Such unsaturated compounds, obtained from various sources such as the conversion of or extraction from refinery streams produced in the modern integrated refinery sometimes termed a petrocomplex, are still relatively cheap chemicals and upgrading thereof has economic advantages.

BRIEF DESCRIPTION OF THE INVENTION

I have discovered that a catalyst system comprising an alkali metal compound and a sulfur source comprising elemental sulfur or sulfur halide, optionally with a halide source, is effective to oxidize in carboxylic acid media an unsaturated reactant selected from conjugated diolefins and monoolefins to diesters.

My process and catalyst system in one aspect provide for the conversion of cyclic or acyclic monoolefins to saturated cyclic or acyclic vicinal diesters. In a further aspect, my process and catalyst system provided for the conversion of cyclic or acyclic conjugated diolefins to unsaturated diesters.

DETAILED DESCRIPTION OF THE INVENTION

Unsaturated Reactant

The unsaturated reactants which can be converted according to my process and catalyst are selected from conjugated dienes and monoolefins. While mixtures of two or more of either or both of these can be employed, preferably and usually single species are employed to limit subsequent purification steps.

The monoolefins can be either acyclic or cyclic, substituted or unsubstituted, and there does not appear to be any operability limitation on molecular size other than convenience and availability.

The acyclic monoolefins, preferably of 2 to 16 carbon atoms per molecule for convenience and availability, correspond to the general formula:

$$\begin{array}{c} R \quad R \\ | \quad | \\ R-C=C-R \end{array} \quad (I)$$

The cyclic monoolefins, preferably of 4 to 16 carbon atoms per molecule for convenience and availability correspond to the general formula:

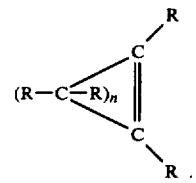

The conjugated diolefin can be either acyclic or cyclic, substituted or unsubstituted, and there does not presently appear to be any limitation on molecular size except convenience and availability.

The acyclic conjugated diolefins, preferably of 4 to 16 carbon atoms per molecule for convenience and availability, correspond to the general formula:

$$\begin{array}{c} R-C=C-C=C-R \\ | \quad | \quad | \quad | \\ R \quad R \quad R \quad R \end{array} \quad (III)$$

The cyclic conjugated diolefins, preferably of 5 to 16 carbon atoms per molecule for convenience and availability, correspond to the general formula:

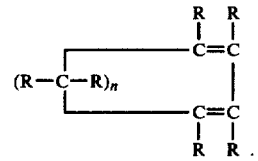

In each of the above formulae, each R is individually selected from hydrogen, halogen, cyano, —COOR', and a hydrocarbyl radical containing preferably not over 12 carbon atoms and which can be alkyl, aryl, cycloalkyl, or combination thereof such as aralkyl, alkaryl, or the like. R' is hydrogen, or an alkyl or aryl radical of preferably not over 10 carbon atoms. The n is an integer of preferably 1 to 14, within the carbon atom limitations described.

Exemplary acyclic monoolefins include ethylene, propylene, 1-butene, 2-butene, 1-hexene, 2-octene, 1-decene, 3-dodecene, 1-hexadecene, 2,3-dimethyl-2-butene, 1,1-diphenylethylene, 1-chloro-2-butene, 3-butenenitrile, ethyl cinnamate, and the like. Exemplary cyclic monoolefins include vinylcyclohexane, cyclobutene, cyclopentene, cyclohexene, cycloheptene, cyclooctene, cyclododecene, 1-methyl-1-cyclopentene, 1-phenyl-1-cyclohexene, ethyl 1-cyclohexene-1-carboxylate, 1,3,4,5,6-pentachlorocyclohexene, 1-cyano-1-cyclohexene, and the like.

Exemplary acyclic conjugated diolefins include: 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decyloxycarbonyl-1,3-butadiene, 2-phenoxycarbonyl-1,3-butadiene, 2-(1-naphthyloxy)carbonyl-1,3-butadiene, 2-benzyl-1,3-butadiene, 2-p-tolyl-1,3-butadiene, 2-chloro-3-methyl-1,3-butadiene, and the like.

Exemplary of the cyclic conjugated diolefins include 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 2-cyclohexyl-1,3- butadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, 2-p-tolyl-1,3-cyclohexadiene, and the like.

It is presently preferred that either the monoolefin reactant or the conjugated diolefin reactant contain only carbon and hydrogen because of availability and reactivity considerations.

Catalyst System

The process of my invention is carried out employing a catalyst system comprising (A) an inorganic sulfur source comprising elemental sulfur, a halide of sulfur, or mixture; and (B) an alkali metal compound, optionally and preferably including a further halide. Presently preferably the catalyst system consists essentially of these components.

The elemental sulfur can be employed in any of its various known forms, though it is presently preferred that a form be utilized which can be easily dispersed in finely divided form in the reaction mixture. Exemplary sulfur halides include sulfur monochloride($S_2Cl_2$), sulfur dichloride($SCl_2$), and sulfur monobromide($S_2Br_2$), and mixtures thereof. Because of convenience in handling, low cost, and availability, elemental sulfur presently is preferred as the sulfur catalyst component.

Any alkali metal compound can be used so long as it is suitable and effective, and is sufficiently soluble in the media as to contribute the desired alkali metal ion. The alkali metal can be one or more of lithium, sodium, potassium, or cesium. Suitable alkali metal compounds include the halides, nitrates, carboxylates, oxides, sulfides, and hydroxides.

Exemplary alkali metal compounds include lithium chloride, lithium bromide, lithium iodide, lithium acetate, lithium benzoate, lithium octadecanoate, lithium oxide, lithium nitrate, lithium sulfide, and the like; as well as the corresponding sodium, potassium, rubidium, and cesium salts; and the like; and mixtures thereof.

It is optional though presently preferred to include in my catalyst system and in my process a source of halide ion, specifically chloride or bromide ion. It presently appears that the halide ion source provides somewhat improved yields of esters obtained in my process. The halide ion can be provided by the sulfur halide component, by the alkali metal compound, or by both, or a separate source of further halide ion can be added to the reaction system. Such additional sources include haloolefin compounds such as the dihalobutenes and allyl halides.

The catalyst of the instant invention can be further described in terms of the ratio of sulfur as free sulfur or the sulfur in the sulfur halide compound to the alkali metal compound component of the catalyst. The ratios can range widely, so long as effective for the oxidation results desired. This ratio can be conveniently expressed in terms of an atom ratio of sulfur to alkali metal. Presently considered exemplary is an atom ratio in the range of about 1:0.1 to 1:20, preferably about 1:1 to 1:8.

The amount of catalyst employed in the process of my invention can be expressed in terms of the molar ratio of unsaturated reactant to gram equivalents of sulfur in the catalyst system. The ratios can range widely, so long as effective for the oxidation results desired. Presently considered exemplary is a ratio in the range of about 1:1 to 50:1, preferably about 2:1 to 12:1.

Where employed, the amount of halide ion source can be expressed in terms of the gram equivalent ratio of halide ion to sulfur in the catalyst system. The ratios can range widely, so long as effective for the oxidation results desired. Presently considered exemplary is a ratio in the range of about 0.1:1 to 20:1, preferably about 1:1 to 10:1.

Carboxylic Acid Media/Reactant

The term carboxylic acid media includes the use of mono- or dicarboxylic acids alone, or in admixture with each other, or with the anhydrides. The carboxylic acid employed in the process of my invention includes monocarboxylic acids, dicarboxylic acids, or both, preferably of up to 18 carbon atoms per molecule for availability and liquidity under suggested reaction conditions, and most preferably employed in conjunction with an anhydride.

The monocarboxylic acids, preferably of 2 to 18 carbon atoms per molecule, can be characterized by the (V) general formula $R'''$—COOH in which $R'''$ represents an alkyl, cycloalkyl, or aryl radical, and includes halogen, cyano, and —COOR' substituted derivatives thereof in which up to four halogen, cyano, or —COOR' substituents can be present in the $R'''$ group. R' is as previously defined.

The dicarboxylic acids, preferably of 2 to 18 carbon atoms per molecule, can be characterized by the (VI) general formula $R''''(COOH)_2$ in which $R''''$ represents a valence bond, or is an alkylene, cycloalkylene, or arylene radical, and includes halogen, cyano, and —COOR' derivatives thereof in which up to four halogen, cyano or —COOR' substituents can be present in the $R''''$ group. R' is as previously defined.

Exemplary monocarboxylic acids include acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and the like, alone, or in admixture.

Exemplary dicarboxylic acids include oxalic acid, malonic acid, succinic acid, adipic acid, terephthalic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, and the like, alone, or in admixture.

It is optional, though presently preferred, to employ, as part of the reaction mixture, a carboxylic acid anhydride in addition to the carboxylic acid, preferably the corresponding carboxylic acid anhydride. The use of a carboxylic acid anhydride serves to simplify the purification and separation steps by reducing the amount of by-products which contain free hydroxy groups. Exemplary anhydrides include those corresponding to the described acids and need not be individually recited.

The presently preferred carboxylic acid is acetic acid, and presently preferred as a carboxylic acid media of acetic acid/acetic anhydride.

Reaction Conditions

The process of my invention is an oxidation reaction and as such is carried out in the presence of free oxygen. The amount of oxygen present is not believed to be critical, though it is recognized that an undesirably slow reaction will result if the concentration of oxygen is very low. Pure oxygen can be employed, or mixtures of oxygen with inert gases such as air can be employed as a convenient source of free oxygen for my process.

It is recognized that explosive conditions could be attained if the amount of oxygen added to the reaction system is not properly controlled. The process of my invention, as is true with many oxidation reactions, is highly exothermic and this aspect further dictates caution in adding oxygen to the reaction system. Because of these considerations, it is desirable to add the oxygen incrementally or continuously during the reaction to avoid reaching an explosive range of oxygen concentration, and to allow better control of the temperature of the reaction. A reaction vessel with efficient mixing means thus is desirable to avoid build-up of potentially dangerous concentrations of free oxygen.

The process can be carried out under an oxygen pressurization over a broad range, so long as sufficient oxygen is provided to be effective in the oxidation reactions, not cause unduly long times of reaction, and at the same time not be so unduly high in concentration as to provide unduly hazardous conditions. An exemplary broad range of oxygen pressure is about 0.1 to 1.000, presently preferably about 5 to 200, psig of oxygen above autogenous pressure at the temperature employed.

The reactions of my process can be carried out over a broad temperature range, so long as the temperature is sufficient to provide suitable reactivity of the reactants, and not so high as to be unduly hazardous. Exemplary temperatures lie in the range of about 25° C. to 200° C., presently preferably about 70° C. to 150° C.

The reaction time can range widely, as desired or convenient. The overall reaction time depends on the temperature, catalyst activity, and oxygen pressure employed. An exemplary range is about 0.1 to 12 hours.

The reaction of my invention is carried out in contact with carboxylic acid media/reactant which provides the acyl and/or acyloxy moiety of the final product. Although some diacyloxy olefin product can be obtained using a wide range of ratios of carboxylic acid media to unsaturated reactant, it presently is apparent that the best yields can be obtained when the molar ratio of carboxylic acid reactant to unsaturated reactant is at least about 2:1. In this connection, one mole of the corresponding carboxylic anhydride is equivalent to 2 moles of carboxylic acid. Ratios lower than about 1:1 preferably should not be employed due to reduced yields, and ratios considerably higher than 2:1 can be employed, such as up to about 50:1 or higher, since the excess carboxylic acid media then serves as a reaction diluent. The molar ratio of acid:anhydride, where the anhydride is employed, can range widely so long as effective. A suggested ratio is about 1:2 to 4:1, presently preferred about 2:1, by volume.

The process of my invention can be carried out in a batch or continuous fashion, and in the liquid phase or in the gas phase. In a presently preferred embodiment, the process is carried out in a liquid phase. When conducted in the liquid phase, it is preferred that the carboxylic acid media employed in the process of my invention be normally liquid or at least liquid under the conditions employed for the reaction.

Product Recovery

Reaction mixtures obtained in the process of my invention can be readily treated for product recovery. The reaction mixture generally is vented to remove any unreacted oxygen and unsaturated reactant, and then distilled to remove remaining carboxylic acid media. The product remaining then can be treated, such as by distillation, to recover one or more fractions containing the desired saturated vicinal diesters which will be diacyloxy alkanes or diacyloxy cycloalkanes from monoolefin reactants, or in the case of conjugated diolefin reactants will be diacyloxy olefins as products.

In most instances, the catalyst can be recovered from the distillation residue and recycled to the reaction zone as desired. Any unreacted unsaturated reactant recovered from the reaction mixture also can be recycled to the reaction zone as desired.

The diacyloxy olefins recovered from the product mixture include, in many instances, an amount of 1,2- or vicinal isomer which can be recycled to the reaction zone and thereby converted to the more desirable 1,4-diacyloxy olefin.

Products

Saturated cyclic or acyclic vicinal diesters produced from cyclic or acyclic monoolefinic reactants can be represented by general formulae, using reactants as indicated:

| Reactants | | | |
|---|---|---|---|
| Carboxylic Acid | Monoolefin | | Product |
| V | I | $\begin{array}{cc} R & R \\ | & | \\ R-C\!\!-\!\!-\!\!-\!\!-\!\!C-R \\ | & | \\ O & O \\ | & | \\ C\!=\!O & C\!=\!O \\ | & | \\ R'' & R'' \end{array}$ | (VII) |
| VI | I | $\begin{array}{cc} R & R \\ | & | \\ R-C\!\!-\!\!-\!\!-\!\!-\!\!C-R \\ | & | \\ C\!=\!O & C\!=\!O \\ | & | \\ R''' & R''' \\ | & | \\ CO_2H & CO_2H \end{array}$ | (VIII) |

| Reactants | | Product |
|---|---|---|
| Carboxylic Acid | Monoolefin | |
| V | II | (IX) $\begin{array}{c}\text{R}\\\text{(R—C=R)}_n\end{array}\Big\langle\begin{array}{c}\text{C—O—C(=O)—R''}\\\text{C—O—C(=O)—R''}\end{array}$ |
| VI | II | (X) $\begin{array}{c}\text{R}\\\text{(R—C=R)}_n\end{array}\Big\langle\begin{array}{c}\text{C—O—C(=O)—R'''—CO}_2\text{H}\\\text{C—O—C(=O)—R'''—CO}_2\text{H}\end{array}$ |

Specific examples of saturated cyclic or cyclic vicinal diesters represented by the above formulae include (VII) ethylene diethanoate, ethylene dioctadecanoate, 2,3-butylene bis(2-ethylhexanoate), 1-cyano-2,3-propylene bis(4-chlorobenzoate), and 1,2-hexadecenyl bis(trichloroacetate); (VIII) ethylene di(hydrogen succinate), 1-chloro-2,3-butylene di(hydrogen oxalate); cyclohexylethylene di(hydrogen adipate), 3,4-dodecylene di(hydrogen terephthalate), (IX) 1,2-cyclobutylene diethanoate, 1,2-cyclohexylene bis(chloroacetate), 1,2-cyclododecylene bis(2-bromobutanoate), and 1-cyano-1,2-cyclohexylene diethanoate; (X) 1,2-cyclopentylene di(hydrogen malonate), 1,2-cyclooctylene di(hydrogen adipate), 1,2-cyclododecylene di(hydrogen terephthalate), 1-phenyl-1,2-cyclohexylene di(hydrogen oxalate), and 1-methyl-1,2-cyclopentylene di(hydrogen succinate).

Unsaturated diesters produced from cyclic or acyclic conjugated diolefins can be represented by general formulae, using reactants as indicated:

| Reactants | | Product |
|---|---|---|
| Carboxylic Acid | Conjugated Diolefin | Diacyloxy Olefin |
| V | III | (XI) $\begin{array}{c}\text{R—C(R)(O—C(=O)—R''')—C(R)=C(R)—C(R)(O—C(=O)—R''')}\end{array}$ |
| VI | III | (XII) $\begin{array}{c}\text{R—C(R)(O—C(=O)—R''''—CO}_2\text{H)—C(R)=C(R)—C(R)(O—C(=O)—R''''—CO}_2\text{H)}\end{array}$ |
| V | IV | (XIII) $\begin{array}{c}\text{R}\\\text{(R—C=R)}_n\end{array}\Big\langle\begin{array}{c}\text{C(R)—O—C(=O)—R'''}\\\text{C—R}\\\text{C—R}\\\text{C(R)—O—C(=O)—R'''}\end{array}$ |
| VI | IV | (XIV) $\begin{array}{c}\text{R}\\\text{(R—C=R)}_n\end{array}\Big\langle\begin{array}{c}\text{C(R)—O—C(=O)—R''''—CO}_2\text{H}\\\text{C—R}\\\text{C—R}\\\text{C(R)—O—C(=O)—R''''—CO}_2\text{H}\end{array}$ |

General formulae XI, XII, XIII, and XIV represent only the predominant diacyloxy olefin product obtained in the reactions indicated. These products generally are accompanied by relatively smaller amounts of isomeric diacyloxy olefins. For example, using general formula XI as an illustration, the isomeric product can be represented by the general formula:

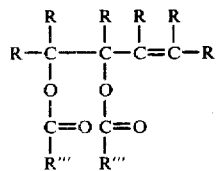

Specific examples of cyclic or acyclic unsaturated diesters represented by the above formulae include (XI) 1,4-diacetoxy-2-butene, 1,4-diacetoxy-2-hexadecene, 1,4-dioctanoyloxy-2-chloro-3-methyl-2-butene, 1,4-di(-trichloroacetoxy)-2-cyano-2-butene, and 1,4-dibenzoyloxy-2-ethoxycarbonyl-2-butene; (XII) 1,4-butene-2-diyl di(hydrogen oxalate), 1,4-butene-2-diyl di(hydrogen adipate), 2-chloro-3-methyl-1,4-butene-2-diyl di(hydrogen succinate), and 1,4-hexadecene-2-diyl di(hydrogen terephthalate); (XIII) 3,5-diacetoxycyclopentene, 3,6-di(chloroacetoxy)cyclohexene, 3,8-di(cyanoacetoxy)cyclooctene, 3,12-diacetoxycyclododecene, 3,8-butanoyloxy-4,5,6,7-tetrabromocyclooctene, and 3,5-di(trichloroacetoxy)hexachlorocyclopentene; (XIV) 3,5-cyclopentenediyl di(hydrogen oxalate), 3,8-cyclooctenediyl di(hydrogen succinate), 3,6-cyclohexenediyl di(hydrogen adipate), and 3,12-cyclododecenediyl di(hydrogen terephthalate).

EXAMPLES

The following examples are intended to assist one skilled in the art to a further understanding of the invention. Particular species, amounts, and relationships, are intended to be exemplary and not limitative of the scope of my invention.

EXAMPLE I

Runs were conducted using a 250 ml Fisher-Porter aerosol compatability bottle equipped with a magnetic stirrer means. In each run the reactor bottle was charged with the catalyst materials, 1,3-butadiene as the unsaturated reactant, and a carboxylic acid media reactant/diluent as indicated in Table I below.

After the bottle reactor was charged with the ingredients it was placed in an oil bath, pressured to 30 psig with oxygen, and heated to 140° C. Typically, about 1.5 hours was required to reach the desired reaction temperature after which the reaction was continued for about 6 hours. During each run the reactor was pressured intermittently with oxygen to 130 psig at about 10–30 minute intervals.

At the conclusion of the reaction the reactor bottle was cooled, vented, and weighed to determine the weight gain (oxygen pick-up) that had occurred during the oxidation reaction. The reaction mixture in each run then was transferred to a distillation flask and distilled through an 18 inch Vigreux column to obtain two fractions. The first fraction was essentially acetic acid or an admixture of acetic acid and acetic anhydride. The second fraction contained small amounts of acetic acid and/or acetic anhydride and the diacyloxy olefins. Gas-liquid phase chromatograph (GLC) analysis of both fractions generally was carried out to identify the components and the amounts present in said fractions. Table I below shows the amounts of catalyst ingredients utilized in each run and other reaction conditions, and Table II presents the results obtained in each run.

Table I

| Run | S, mg-eq. | LiX[a] (mmol) | DHB,[b] (mmol) | AcOH[c] ml | Ac₂O[d] ml | 1,3-Bd[e] (mmol) |
|---|---|---|---|---|---|---|
| 1 | 43.7 | LiBr (75) | DBB (10.7) | 50 | 25 | 209.2 |
| 2[f] | 43.7 | LiBr (75) | DBB (10.7) | 50 | 25 | 222.2 |
| 3 | 21.8 | LiBr (112.5) | DBB (10.7) | 50 | 25 | 209.3 |
| 4 | 43.7 | LiBr (75) | DBB (10.7) | 0 | 75 | 225.9 |
| 5[g] | 43.7 | LiBr (75) | DBB (10.7) | 50 | 25 | 212.9 |
| 6 | 43.7 | LiCl (75.3) | DCB (11.3) | 50 | 25 | 210.3 |

[a]LiX = LiBr or LiCl as indicated.
[b]DHB = dihalobutene; DBB is 1,4-dibromo-2-butene, and DCB is 1,4-dichloro-2-butene.
[c]AcOH = acetic acid.
[d]Ac₂O = acetic anhydride.
[e]1,3-Bd = 1,3-butadiene.
[f]Run 2 was carried out at 120° C.
[g]Run 5 was carried out with 25 ml acetonitrile added to the reaction mixture and with repressuring with oxygen during the run to 120 psig.

Table II

| Run | 1,2-DAB[h] mmol | c-1,4-DAB[i] mmol | t-1,4-DAB[j] mmol | DAB[k] % Yield |
|---|---|---|---|---|
| 1 | 17.3 | 12.6 | 50.4 | 38.4 |
| 2 | 40.4 | 6.3 | 28.3 | 33.8 |
| 3 | 8.3 | 2.9 | 5.8 | 8.1 |
| 4 | 9.3 | 12.3 | 48.8 | 31.2 |
| 5 | (Not analyzed, apparent low yield) | | | |
| 6 | 6.5 | 1.0 | 3.5 | 5.2 |

[h]1,2-DAB = 1,2-diacetoxy-3-butene.
[i]c-1,4-DAB = cis-1,4-diacetoxy-2-butene.
[j]t-1,4-DAB = trans-1,4-diacetoxy-2-butene.
[k]Yield of combined diacetoxybutenes based on amount of 1,3-butadiene charged.

Cause of the low yields of diacetoxybutenes in Runs 3 and 6 are not presently known. The apparent low yield in Run 5 shows the deleterious effect of including acetonitrile in the reaction mixture. Runs 1, 2, and 4 show good yields of diacetoxybutenes in accordance with my invention.

EXAMPLE II

In the same type of apparatus as employed in the runs of Example I above, another run (Run 7) was carried out in which the reactor was charged with 3.2 grams (75.3 mmol) of lithium chloride, 75 ml of acetic anhydride, 2.8 grams (22.5 mmol) of 1,4-dichloro-2-butene, 3.1 grams (48.4 mmol) of sulfur dioxide, and 11.5 grams (212.9 mmol) of 1,3-butadiene in the vapor phase. The bottle reactor was placed in an oil bath, pressured to 30 psig with oxygen and heated to 140° C. About 1.5 hours were required to reach the desired reaction temperature after which the reaction was continued for 5.5 hours. During the reaction the bottle reactor was pressured to 130 psig with oxygen at about 10–30 minute intervals.

At the end of the reaction the bottle reactor was cooled, vented, and weighed to indicate a weight gain of 2.0 grams. The reaction mixture was transferred, using 14.0 grams of additional acetic anhydride, to a distillation flask and distilled through an 18 inch Vigreux column. The overhead, acetic acid and acetic anhydride, which boiled within a range of 44°–65° C. at 50 mm mercury pressure weighed 89.1 grams, but there was substantially no liquid residue in the flask following the recovery of this overhead material.

Run 7 demonstrates that essentially no formation of diacetoxybutenes occurred in the presence of sulfur dioxide as the sulfur-containing component of the catalyst system.

EXAMPLE III

Runs 8–13 were carried out according to the process of my invention utilizing 1,3-butadiene as the unsaturated reactant, and with elemental sulfur and alkali metal compounds as catalyst. The runs of this Example did not include a source of halide ion in the catalyst system. Run 8 was carried out in the same type of apparatus as described in Examples I and II. Runs 9–13 were carried out in one liter stirred reactors. Run 9 used a glass-lined reactor, and Runs 10–13 used a reactor made of Hastelloy metal. Substantially the same procedure was utilized in each of the runs of this Example as described in Example I.

In Run 9, the reactor was vented, opened, and the reaction mixture transferred to a distillation flask and the acetic acid distilled away at 50 mm mercury pressure. There was recovered 310.5 grams in this distillation as overhead material. The distillation residue was distributed between diethyl ether and water, filtered through Celite to remove some black carbonaceous solid, and the layers separated. The aqueous layer was extracted with diethyl ether and the combined diethyl ether extracts were washed with sodium carbonate solution, dried over anhydrous magnesium sulfate, filtered, and the diethyl ether removed by distillation to give 34.4 grams of an oily material. The acetic acid solution was neutralized with sodium carbonate, dried over anhydrous magnesium sulfate, filtered, and diethyl ether removed to give 14.5 grams of additional oily material. Each of these recovered oily fractions was analyzed by gas-liquid phase chromatography. Results are shown in Table IV.

In Runs 8 and 10–13, the reactor was vented, opened, and the product transferred to a distillation flask. Unreacted 1,3-butadiene was removed at 50 mm mercury pressure followed by the collection of two fractions. Fraction 1 typically boiled from about 40° to 80° C. at 50 mm mercury, while Fraction 2 typically boiled at about 60° to 130° C. at 8 mm mercury. Fraction 1 in each of these runs was essentially acetic acid and/or acetic anhydride, while Fraction 2 consisted essentially of the diacetoxybutenes.

Fraction 2 in each of Runs 8 and 10–13 was analyzed by gas-liquid phase chromatography to determine the composition of said fraction.

Table III shows the amounts of catalyst ingredients and 1,3-butadiene charged in each of the runs along with the reaction conditions. Table IV shows the results obtained in Runs 8–13.

Table III

| Run No. | S mg-eq. | Li Compound mmol | AcOH ml | Ac$_2$O ml | 1,3-Bd mmol | Temp. °C. |
|---|---|---|---|---|---|---|
| 8 | 43.7 | 75$^{(a)}$ | 0 | 75 | 212.6 | 140 |
| 9 | 81.1 | 225$^{(a)}$ | 75 | 150 | 925.9 | 140 |
| 10 | 81.1 | (23g)$^{(b)}$ | 75 | 150 | 907.4 | 100 |
| 11 | 18.7 | 200$^{(a)}$ + 10$^{(c)}$ | 75 | 150 | 935.2 | 140 |
| 12 | 40.5 | 50$^{(d)}$ | 150 | 75 | 1,037 | 140 |
| 13 | 40.5 | $^{(e)}$ | 150 | 75 | 1,055 | 140 |

$^{(a)}$Lithium acetate dihydrate.
$^{(b)}$Lithium acetate (purified). Hydrated state not known.
$^{(c)}$Lithium nitrate.
$^{(d)}$Lithium sulfide.
$^{(e)}$Cupric acetate monohydrate, 50 mmol.

Table IV

| Run No. | 1,2-DAB mmol | c-1,4-DAB mmol | t-1,4-DAB mmol | DAB % Yield |
|---|---|---|---|---|
| 8 | 31.4 | —$^{(f)}$ | 5.1 | 17.2 |
| 9 | 77.8 | 4.8 | 28.7 | 12 |
| 10 | 104.9 | (47.5)$^{(g)}$ | | 16.8 |
| 11 | 82.5 | 3.4 | 9.1 | 10.2 |
| 12 | 76.9 | (25.6)$^{(g)}$ | | 9.9 |
| 13 | (Analysis not conducted due to low yield). | | | |

$^{(f)}$Not detected in GLC analysis.
$^{(g)}$Separate determination of cis- and trans- isomer content not carried out.

Comparison of the results of Table IV with those of Table II indicate that it is preferred to utilize a halide ion source in the catalyst system of this invention in order to achieve higher diacetoxybutene yields. The low yield of Run 13 shows that a copper compound is not a suitable replacement for the alkali metal compound catalyst component of my invention.

EXAMPLE IV

Runs 14 and 15 were carried out according to the process of my invention using trans-2-butene as the unsaturated reactant. These runs utilized the one liter glass-lined reactor as the reaction vessel as described in Example III, 150 ml of acetic anhydride and 75 ml of acetic acid as the carboxylic acid media reactant/diluent system, and a catalyst composed of 2.6 grams (81.1 milligram equivalents) of powdered sulfur and 225 mmol of lithium bromide. In each Run 14 and 15 the autoclave was pressured to about 60 psig with oxygen initially and then heated to about 140° C. About 0.75 hours was required to reach the desired reaction temperature after which the reaction was continued for about 3.5 hours. During each run the reactor was repressured to about 220 to 350 psig with oxygen at about 30 minute intervals.

At the conclusion of the reaction for Run 14, the autoclave was cooled, vented, and the reaction mixture transferred to a distillation flask and distilled through an 18 inch Vigreux column to recover two fractions. Fraction 1 boiling from 41° to 75° C. at 58 mm mercury pressure weighed 276.8 grams, while Fraction 2 boiling at 75° to 110° C. at 58 mm mercury pressure weighed 39.0 grams. Fraction 2 appeared to contain some acetic acid so it was taken up in diethyl ether, washed with sodium carbonate, and dried over anhydrous magnesium sulfate and then filtered. The diethyl ether was removed by distillation to give 28.2 grams of a pale yellow oil. Fraction No. 1 also was neutralized with sodium carbonate and then extracted into diethyl ether. The diethyl ether extracts were dried over anhydrous magnesium sulfate, filtered, and the diethyl ether removed by distillation to give 34.8 grams of pale yellow oil. Each of the oily residues from the fractions above were analyzed by gas-liquid phase chromatography combined with mass spectral analysis.

The reaction mixture obtained in Run 15 was treated in essentially the same manner as that described for Run 14 with the exception that the second fraction obtained on the initial distillation was not treated with diethyl ether. The products recovered from the diethyl ether extraction of sodium carbonate neutralized fraction 1 and fraction 2 were analyzed as described for the products of Run 14 above. The results of Runs 14 and 15 are shown below in Table V.

Table V

| Run No. | trans-2-Butene mmol | 2,3-DABA[a] mmol | % Yield[b] 2,3-DABA |
|---|---|---|---|
| 14 | 910.7 | 115 | 12.6 |
| 15 | 910.7 | 88 | 9.6 |

[a]2,3-DABA = 2,3-diacetoxybutane.
[b]Yield based on the amount of trans-2-butene charged. The product mixtures also contained amounts of other compounds such as dibromobutanes (4–8 grams), butenyl acetates (1–4 grams), and unidentified compounds (1–4 grams).

The results shown in Table V demonstrate that the catalyst system of my invention is effective for the production of diacyloxyalkanes from 1-olefins, here diacetoxybutanes from butenes, in the presence of free oxygen and carboxylic acid media, here acetic acid admixed with acetic anhydride. Unreacted unsaturated reactant can be recovered and recycled, if desired.

Utility

The 1,4-diacyloxy olefins have utility as intermediates for the preparation of the corresponding saturated diols, or tetrahydrofuran or substituted tetrahydrofurans. For example, British Pat. No. 1,170,222 describes the preparation of tetrahydrofurans by starting with conjugated diolefins and proceeding through the 1,4-diacyloxybutenes. Tetrahydrofuran itself has wide utility as a solvent, as a randomizing agent in preparation of various copolymers, and the like. The diols prepared from the process of my reaction are useful for conversion to polyesters or polyurethanes, and as solvents or humectants. The substituted tetrahydrofurans are useful as solvents and intermediates in the preparation of diamines or dicarboxylic acids for polyamide preparation.

Starting with the cyclic or acyclic monoolefins, the resulting products in accordance with the process of my invention are saturated or acyclic vicinal diesters. These diesters also can be utilized to provide the resulting corresponding diols, which then are saturated vicinal diols, useful as solvents humectants, monomers for production of polyesters, or polyurethanes, and the like.

The disclosure, including data, has illustrated the value and effectiveness of my invention. The examples, the knowledge and background of the field of the invention and the general principles in chemistry and other applicable sciences, have formed the bases to which the broad description of the invention, including the ranges of conditions and generic groups of operant components have been developed, and have formed the bases for my claims here appended.

I claim:

1. A composition comprising catalytically effective ratios of (A) a sulfur source selected from sulfur, sulfur chlorides, sulfur bromides, and mixtures; and (B) an alkali metal compound; (C) a haloolefin which is a chloroolefin or bromoolefin, and optionally (D) carboxylic acid media.

2. The composition of claim 1 employing an atom ratio of (A) sulfur of said sulfur source to alkali metal of said (B) alkali metal compound in the range of about 1:0.1 to 1:20, and of said (C) halide source where employed in the range of about 0.1:1 to 20:1 gram equivalent ratio of halide ion to sulfur of said (A) sulfur source.

3. The composition according to claim 1 wherein said (B) alkali metal compound is supplied by lithium, sodium, potassium, rubidium, or cesium, chloride, acetate, oxide, nitrate, sulfide, or mixture thereof.

4. The composition of claim 3 wherein said (A) is sulfur; and said (B) is lithium bromide, chloride, acetate, nitrate, or sulfide.

5. The composition of claim 2 wherein said (C) haloolefin is selected from dihalobutenes and allyl halides.

6. The composition of claim 1 wherein said (B) alkali metal compound is at least in part an alkali metal halide.

7. The composition of claim 2 consisting essentially of said (A), (B), and (C).

8. The composition of claim 7 wherein said (A) is sulfur; said (B) is lithium bromide, chloride, acetate, nitrate, or sulfide; and said (C) is bromide and chloride.

9. The composition of claim 7 wherein said (C) is at least in part supplied by 1,4-dibromo-2-butene or 1,4-dichloro-2-butene.

10. The composition of claim 1 consisting essentially of said (A), (B), (C), and (D).

11. The composition of claim 10 wherein said (A) is sulfur, said (B) is lithium bromide, chloride, acetate, nitrate, or sulfide; said (C) is at least one of bromide and chloride; and said (D) is acetic acid, acetic anhydride, or both.

12. The composition of claim 10 wherein said (D) carboxylic acid media is at least one monocarboxylic acid, dicarboxylic acid, an anhydride, or admixture thereof.

13. The composition of claim 12 wherein said (D) carboxylic acid media is selected from the group consisting of mono- and dicarboxylic aliphatic and aromatic acids, their acid anhydrides, and mixtures thereof, having 2 to 18 carbon atoms per molecule.

14. The composition of claim 13 wherein said (D) carboxylic acid media monocarboxylic acid is represented by the formula R'''—COOH, and said dicarboxylic acid is represented by the formula R''''(COOH)$_2$;

wherein R''' is selected from the group consisting of alkyl, cycloalkyl, and aryl radicals, and halogen, cyano and —COOR' substituted derivatives thereof, wherein up to four of said halogen, cyano or —COOR' substituents can be present in said radical; and R'''' is selected from the group consisting of a valence bond and alkylene, cycloalkylene and arylene radicals, and halogen, cyano and —COOR' substituted derivatives thereof wherein up to four of said halogen, cyano or —COOR' substituents can be present in said R'''' radical; and wherein R' is selected from the group consisting of hydrogen, an alkyl radical of up to 10 carbon atoms, and an aryl radical of up to 10 carbon atoms.

15. The composition of claim 14 wherein said (D) carboxylic acid media is selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid; their respective anhydrides; and mixtures thereof.

16. The composition of claim 14 wherein said (D) carboxylic acid media is selected from the group consisting of oxalic acid, malonic acid,
succinic acid, adipic acid, terephthalic acid, tetrabromo-1,4-benzenedicarboxylic acid,
tetracyano-1,4-benzenedicarboxylic acid,
tetramethoxycarbonyl-1,4-benzenedicarboxylic acid,
2-decyloxycarbonylhexanedioic acid; their respective anhydrides; and mixtures thereof.

17. The composition of claim 10 wherein said (A) is sulfur monochloride, sulfur dichloride or sulfur monobromide.

18. The composition of claim 9 wherein said (A) is sulfur; said (B) is lithium bromide, chloride, acetate, nitrate, or sulfide; and said (D) is acetic acid, acetic anhydride, or both.

* * * * *